United States Patent
Poole et al.

(10) Patent No.: US 7,172,587 B2
(45) Date of Patent: Feb. 6, 2007

(54) CATHETER HAVING SELECTIVELY VARIED LAMINATION

(75) Inventors: Matthew S. Poole, Bradford, MA (US); John Horrigan, Beverly, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 398 days.

(21) Appl. No.: 10/434,775

(22) Filed: May 9, 2003

(65) Prior Publication Data

US 2004/0225278 A1  Nov. 11, 2004

(51) Int. Cl.
*A61M 25/00* (2006.01)
(52) U.S. Cl. .................. 604/525; 604/523; 604/524
(58) Field of Classification Search .............. 604/523, 604/264, 272
See application file for complete search history.

(56) References Cited

U.S. PATENT DOCUMENTS

| | | | |
|---|---|---|---|
| 4,356,052 A | | 10/1982 | Moraw et al. |
| 4,441,945 A | | 4/1984 | Moraw et al. |
| 4,636,346 A | * | 1/1987 | Gold et al. ................. 264/139 |
| 5,462,523 A | * | 10/1995 | Samson et al. .............. 604/30 |
| 5,695,483 A | | 12/1997 | Samson |
| 5,755,704 A | | 5/1998 | Lunn |
| 5,964,971 A | | 10/1999 | Lunn |
| 6,004,310 A | | 12/1999 | Bardsley et al. |
| 6,217,565 B1 | | 4/2001 | Cohen |
| 6,344,045 B1 | * | 2/2002 | Lim et al. .................. 606/108 |
| 6,517,765 B1 | * | 2/2003 | Kelley ........................ 264/510 |
| 6,837,890 B1 | * | 1/2005 | Chludzinski et al. ....... 606/108 |
| 2004/0054349 A1 | | 3/2004 | Brightball |

\* cited by examiner

*Primary Examiner*—Nicholas D. Lucchesi
*Assistant Examiner*—Melissa A. McCorkle
(74) *Attorney, Agent, or Firm*—James F. Crittenden

(57) ABSTRACT

A tubular medical catheter having a least one region of selectively varied lamination is provided herein.

17 Claims, 3 Drawing Sheets

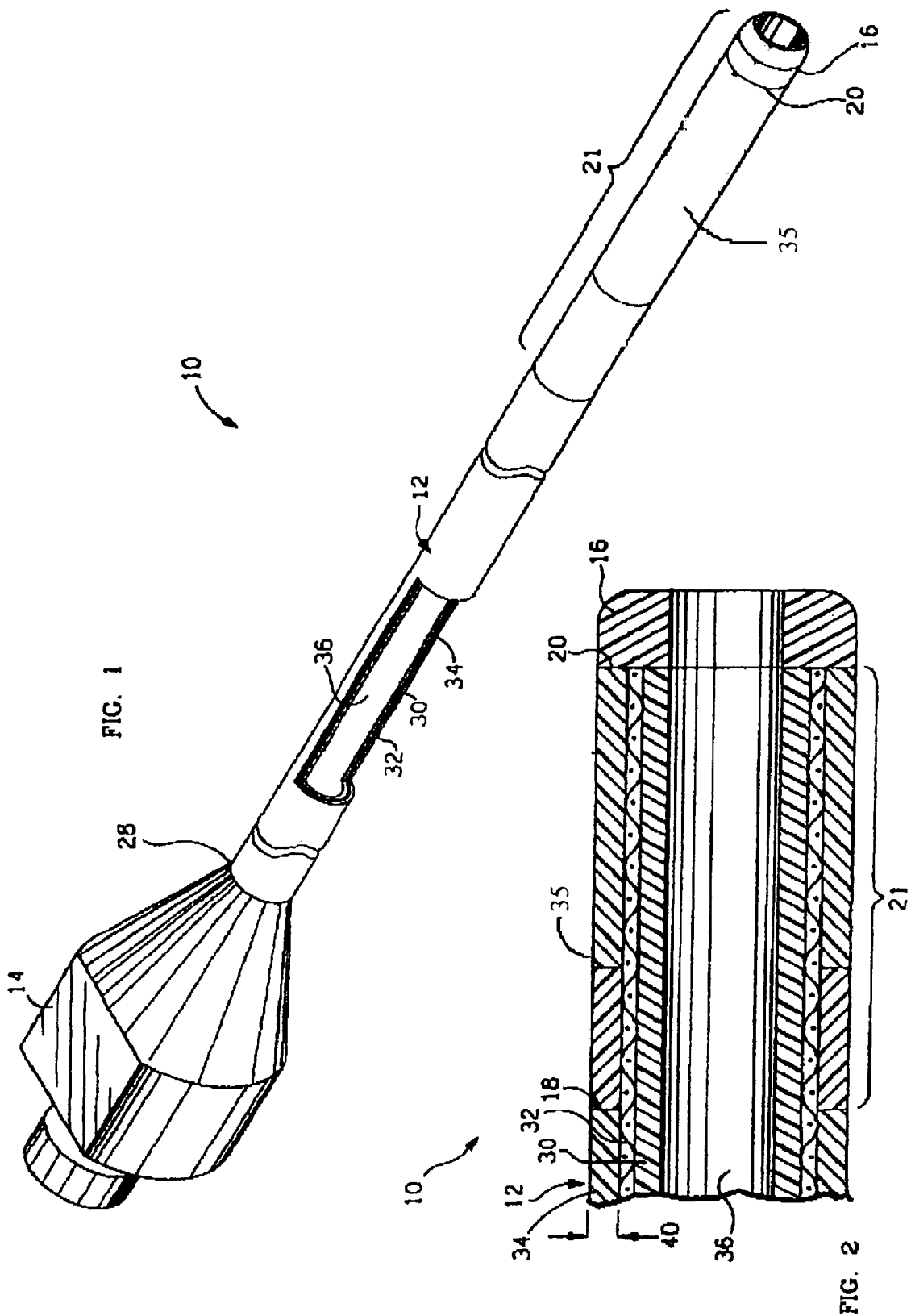

CATHETER HAVING SELECTIVELY VARIED LAMINATION

FIELD OF THE INVENTION

The present invention relates to catheters comprising sections of selectively varied lamination. More specifically, the invention relates to catheters having increased flexibility towards the distal end due to at least one section of selectively varied lamination between the inner liner and outer shell, and methods for making the same.

BACKGROUND OF THE INVENTION

A number of intravascular procedures are currently utilized to treat a stenosis within a body vessel of a human being. A common intravascular procedure is referred to as percutaneous transluminal coronary angioplasty (PTCA or hereinafter "angioplasty"). During a typical angioplasty procedure, a guidewire is initially positioned within the body vessel and a guiding catheter is positioned over the guidewire. Next, a balloon catheter having an inflatable balloon is advanced through the guiding catheter and vessel until the balloon is adjacent to the stenosis. Subsequently, inflation of the balloon compresses the stenosis and dilates the body vessel.

During many diagnostic or interventional catheterization procedures, it is necessary to route the catheter from an entry point, such as either the femoral, brachial or radial artery, to a target location within the vasculature. When properly placing a catheter into position, the catheter should be able to be turned, pulled, and pushed so that the distal end of the catheter can navigate the twists and turns of the blood vessels on its path to the final location. This requires that the catheter be rigid enough to transfer the torque being applied by the operator of the catheter, but also flexible enough so that the catheter will not damage any of the blood vessels of the patient. The catheter can be too stiff, which can prevent the catheter from passing through tortuous blood vessels. Alternately, the catheter can be too soft, which can result in the occurrence of kinks along the length of the catheter. In either of these situations, the usefulness of the catheter in the patient is limited.

In order for intravascular catheters to be neither too stiff nor too soft, it is common to make such catheters with a relatively stiff shaft and a relatively soft distal region. Typically, this variable stiffness is achieved by varying the properties of the materials used to fabricate the catheters. For example, catheters intended for use as angiography catheters or as guiding catheters often comprise a tubular liner surrounded by an outer tubular shell, with a reinforcing layer interposed there between. Either the outer shell or the liner, or both tubular elements may include relatively softer polymeric materials in a distal region of the catheter. Optionally, the reinforcing layer, which is usually a tubular braid, may also have a more flexible, modified form in the distal region.

A problem that has arisen in variable stiffness catheters relates to the challenge of reliable, low-cost manufacturing, especially since many of these devices are discarded after use in only one patient. One fabrication technique taught in the prior art is to make a laminated catheter assembly with uniform polymer materials. Selected regions of the catheter are then modified by radiation treatment to selectively increase stiffness. However, this technique has not become popular due to limitations in the choice of catheter materials and in the control of the final catheter properties. It is therefore more common for intravascular catheters to have a composite construction employing different polymeric materials.

One known technique for manufacturing variable stiffness catheters requires sliding a series of tubular segments having different stiffnesses over an inner assembly comprising a liner surrounded by a reinforcing layer. The tubular segments are shrink-fitted and melt-bonded to the inner assembly using a removable length of heat-shrink tubing. Such a process is tedious and inefficient since catheters can only be fabricated one-at-a-time. In a known reel-to-reel process, outer jacket material is varied by switching between extrusion sources as a length of inner assembly passes through a wire-coating type extruder head. Alternatively, discrete sections of one material are extruded or over-molded onto a length of inner assembly. Then, a different material is extruded onto the length of inner assembly, filling in the spaces between the discrete sections. After forming the continuous, variable-stiffness outer shell, the long assembly is cut into catheter-length sections. Such reel-to-reel processes are more cost-efficient than assembling catheters one-at-a-time. However, the use of different materials to achieve variable catheter stiffness requires multiple assembly steps and/or complex tooling, and the junctions between the different material sections require careful control of design and manufacturing to avoid potentially weak joints that could fail during use.

Accordingly, there is a need for a medical catheter that is simple to manufacture and has varied properties along its length, such as varying catheter stiffness, curve retention, and overall back-up support. The present invention addresses these needs, as well as other problems associated with existing medical catheters. The present invention also offers further advantages over the prior art and solves other problems associated therewith.

SUMMARY OF THE INVENTION

The present invention is directed to medical catheters adapted for use within a body vessel and having variable physical properties along the length of the catheter. The medical catheter comprises a tubular catheter shaft having a distal end that fits within the body vessel. The tubular catheter shaft comprises an inner liner and an outer shell. The medical catheter comprises at least one region of selectively varied lamination between the inner liner and the outer shell.

In some embodiments, at least one region of selectively varied lamination comprises a pattern of laminated sections and non-laminated sections. As examples, the non-laminated sections may be diamond-shaped or oval-shaped, the size of the non-laminated sections may increase towards the distal end, the laminated sections between non-laminated sections may decrease towards the distal end, and/or the non-laminated sections may form circumferentially arranged pairs that can be staggered at 90°. The non-laminated sections increase flexibility of the catheter by intentionally permitting localized movement between the inner liner and the outer shell.

In some embodiments, the distal end of the catheter comprises at least one region of selectively varied lamination, or the proximal end of the catheter comprises at least one region of selectively varied lamination, or the region of selectively varied lamination is present throughout the length of the catheter.

The present invention is also directed to methods for making a medical catheter comprising at least one region of selectively varied lamination. In some embodiments, where the inner liner and outer shell can form a thermal bond, a thermal bond inhibiting agent, such as an ink or wax, is applied in a pattern to selectively inhibit thermal bonding, thus creating at least one non-laminated section. Alternately, a thermoplastic tie layer may be used to thermally bond an inner liner and an outer shell having otherwise incompatible surfaces. A pattern of gaps can be introduced into such a tie layer to produce laminated sections and non-laminated sections. In other embodiments, the inner liner and outer shell are laminated with adhesive instead of a thermal bond. The adhesive may be selectively applied to create a pattern of laminated sections and non-laminated sections. In embodiments where the inner liner requires etching or other preparation to foster adhesive bonding, the etching of the inner liner may be selectively applied or prevented, as by masking in at least one region of the inner liner.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view, in partial cutaway, of a medical catheter having features of the present invention;

FIG. 2 is an enlarged cutaway view of a portion of the medical catheter of FIG. 1;

DETAILED DESCRIPTION OF THE INVENTION

The present invention is directed to a catheter that has at least one region of selectively varied lamination. Any multi-layered medical catheter can be modified to have regions of selectively varied lamination. The catheters described herein are merely exemplary and the invention should not be construed to be limited to only the catheters described herein.

Figure 4:
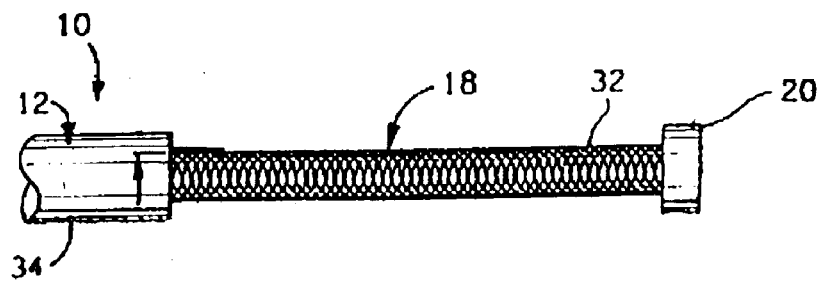
FIG. 4 is an enlarged side plan assembly view illustrating a grooved portion of a catheter shaft in accordance with the present invention.

Referring to FIGS. 1, 2, and 4, a first embodiment of medical catheter 10 having features of the present invention includes tubular catheter shaft 12, hub 14, and tubular flexible tip 16. Catheter shaft 12 can optionally include groove 18, which is cut out of catheter shaft 12 near distal end 20 of catheter shaft 12.

Figure 3:
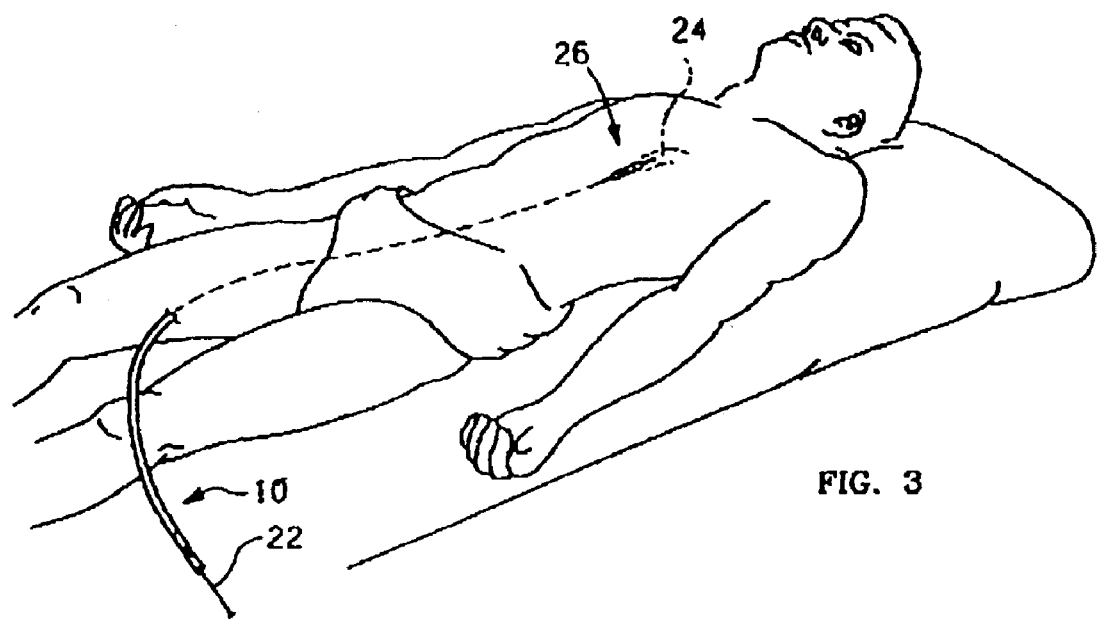
FIG. 3 is a perspective illustration of the inventive medical catheter positioned within a patient.

Medical catheter 10 illustrated herein is utilized to guide an interventional catheter (not shown) and is commonly referred to as a guiding catheter. FIG. 3 illustrates a portion of medical catheter 10 and guidewire 22 positioned in body vessel 24 of patient 26 during a procedure. The location of entry into patient 26 and the location of distal end 20 in patient 26 are merely exemplary.

Referring back to FIGS. 1 and 2, hub 14 is secured to proximal end 28 of catheter shaft 12 while flexible tip 16 is secured to distal end 20 of catheter shaft 12. The physician manipulates hub 14 and proximal end 28 to position medical catheter 10 in body vessel 24. Flexible tip 16 assists in guiding medical catheter 10 in body vessel 24 and minimizes the trauma to vessel 24 and coronary ostium (not shown).

Flexible tip 16 is made of a relatively soft material when compared to the catheter shaft 12. Suitable materials for flexible tip 16 may include polymers such as a polyether block amide ("PEBA") having a hardness of about 40 Shore D. Depending upon the materials utilized, hub 14 and flexible tip 16 can be thermally bonded or attached with an adhesive (not shown) to catheter shaft 12. Those skilled in the art will recognize alternate ways to attach hub 14 and flexible tip 16 and that alternate materials can be utilized for flexible tip 16.

In the embodiment illustrated in FIGS. 1 and 2, tubular catheter shaft 12 includes inner liner 30, optional reinforcing section 32, and outer shell 34. Further, when the catheter comprises groove 18, fill section 35 may be positioned in groove 18. Inner liner 30 is tubular and defines lumen 36, which is sized and shaped to receive, for example, guidewire 22 and subsequently an interventional catheter (not shown). Typically, inner liner 30 is manufactured by extruding a polymer such as PEBA, nylon, polytetrafluoroethylene (PTFE), high density polyethylene (HDPE), or fluorinated ethylene propylene (FEP), which provide good catheter flexibility and movement of guidewire 22 there within. The composition of the inner liner, however, is not limited to these polymers and any suitable polymer can be used so that the catheter has the desired properties. A suitable inner liner 30 has an inner diameter of between about 0.06 and 0.09 inches and an inner liner thickness of about 1.0–1.5 mils. A lubricious coating (not shown) may be added to lumen 36 of inner liner 30 to facilitate movement of inner liner 30 over guidewire 22 and the interventional catheter within lumen 36.

Reinforcing section 32 enhances the torsional strength and prevents or reduces kinking of catheter shaft 12 during movement of medical catheter 10 in body vessel 24. Reinforcing section 32 is embedded between inner liner 30 and outer shell 34 and is substantially coaxial with inner liner 30 and outer shell 34. Reinforcing section 32 may be formed by braiding wire mesh around inner liner 30. Subsequently, outer shell 34 is formed around reinforcing section 32 by applying materials making up the outer shell.

In some embodiments, inner liner 30 and/or outer shell 34 comprise unfilled or low-loaded thermoplastic polymers. For example, inner liner 30 and outer shell 34 each, independently, may include a radiopaque material and/or filler and/or colorant, such that the total content of the radiopaque material and/or filler and/or colorant in inner liner 30 and/or outer shell 34 is between about 0.1% and about 10%, or between about 0.1% and about 5%, or between about 0.1% and about 2% of the total weight making up inner liner 30 and/or outer shell 34. In some embodiments, inner liner 30 and outer shell 34 each, independently, may exclude a radiopaque material and/or filler and/or colorant, thus having 0% by weight of the total weight making up inner liner 30 and/or outer shell 34. An unfilled inner liner 30 and/or outer shell 34 have the advantages of retaining mechanical integrity and modulus of elasticity.

Outer shell 34 provides support to catheter shaft 12 and covers reinforcing section 32 to protect body vessel 24 from reinforcing section 32. Further, outer shell 34 prevents reinforcing section 32 from unwrapping. Outer shell 34 is tubular and coaxial with inner liner 30 and optional reinforcing section 32. A suitable outer shell 34 has an inner diameter of about 0.1 inches and wall thickness 40 of about 1.5–2.5 mils.

Typically, outer shell 34 is manufactured by extruding a polymer over the reinforcing section 32. A suitable shell material for outer shell 34 is a nylon sold under the trademark "TROGAMID" by Creanova (Somerset, N.J.). The shell material may have a hardness of approximately 81 Shore D. Additionally, a lubricious coating (not shown) may be added to outer shell 34 to facilitate movement of catheter shaft 12 within vessel 24.

Those skilled in the art will recognize alternate ways to manufacture inner liner 30, reinforcing section 32, and outer shell 34 and that alternate materials can be utilized for inner liner 30, reinforcing section 32, and outer shell 34. Those skilled in the art will also recognize alternate ways to apply reinforcing section 32 on inner liner 30.

The catheters of the invention comprise at least one region of selectively varied lamination. As used herein, the term "region" refers to a site or location on catheter shaft 12. Region(s) of selectively varied lamination can be located on the distal end of the catheter, the proximal end of the catheter, on any location there between, or any combination thereof. Additionally, the region(s) of selectively varied lamination can be located throughout the entire catheter. Each region(s) of selectively varied lamination can be laid down in a particular pattern comprising laminated sections and non-laminated sections. Non-laminated sections include those sections having no lamination as well as those sections having reduced lamination. For example, the pattern of lamination can be in longitudinal non-laminated strips along the length of the catheter without going around the circumference of the catheter. Alternately, regions of selectively varied lamination can form continuous or non-continuous non-laminated rings around the circumference of the catheter.

Figure 5:
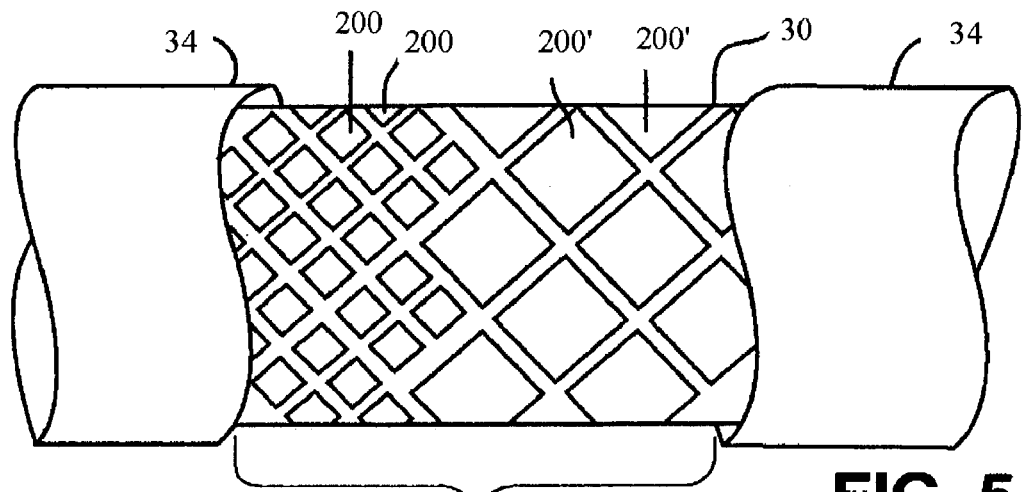
FIGS. 5–7 illustrate catheters in accordance with the present invention, wherein sections of the outer shell have been removed to show a variety of regions of selectively varied lamination.
Figure 6:
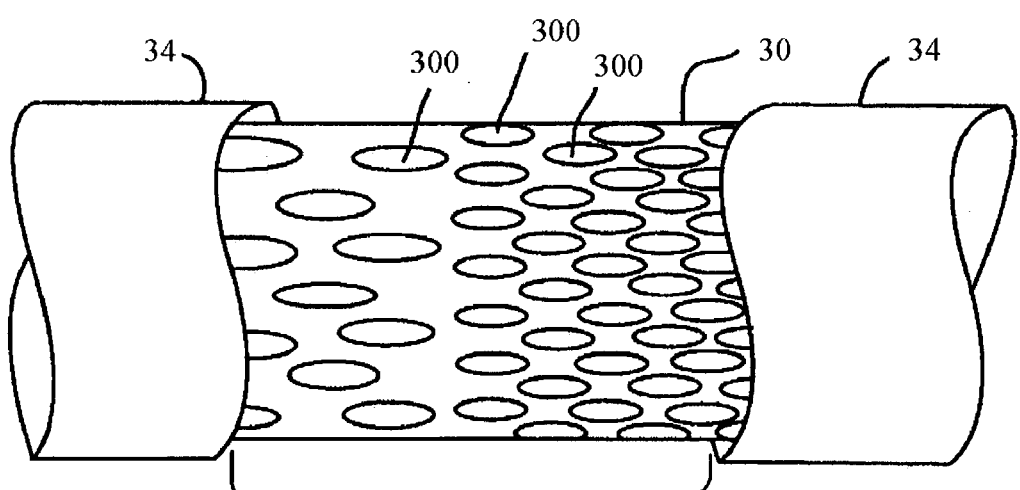
Figure 7:
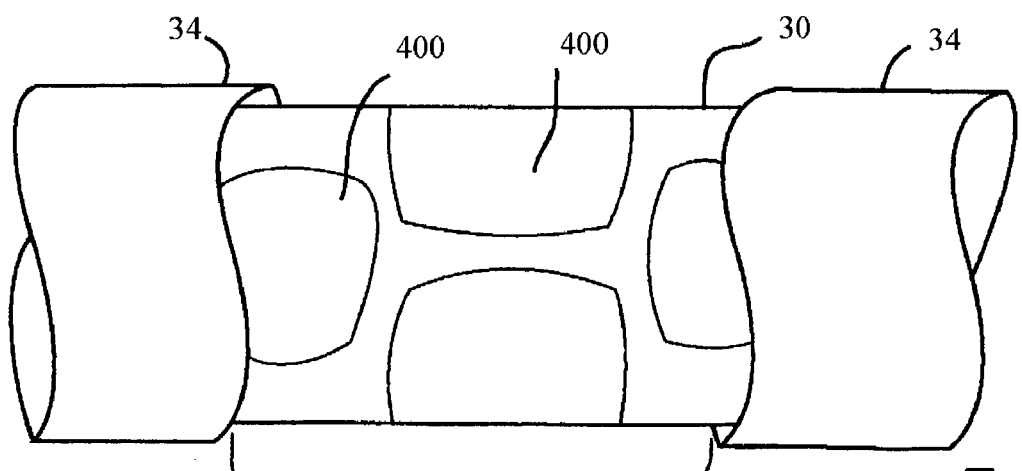

FIGS. 5–7 illustrate a variety of patterns of regions of selectively varied lamination formed in accordance with the invention. In FIG. 5, non-laminated sections 200, 200' in pattern 160 are diamond-shaped, and pattern 160 varies to change the physical properties along the length of the catheter. The portions of pattern 160 between non-laminated sections 200, 200' represent sections that are laminated to bond inner liner 30 to outer shell 34. Larger non-laminated sections 200' in pattern 160 provide decreased laminated areas and corresponding greater flexibility in comparison to smaller non-laminated sections 200. Non-laminated sections 200' may be disposed distal to non-laminated sections 200 to create a more flexible distal region of the catheter. Alternatively, pattern 160 can be reversed, such that sections 200, 200' would represent diamond-shaped laminated portions and the portions between the diamond shapes would not be laminated. In such an arrangement, the relative flexibility of regions comprising sections 200 and 200' would also be reversed.

In FIG. 6, non-laminated sections 300 in pattern 260 are oval or elliptical in shape and pattern 260 varies along the catheter. In pattern 260, all non-laminated sections 300 are of the same size and shape, but the spacing between non-laminated sections changes. In this case, the contracted spacing creates greater flexibility in selected, e.g. distal, portions of the catheter. As mentioned in the previous example, pattern 260 can be reversed, such that sections 300 would represent laminated sections and the portions between the oval or elliptical shapes would not be laminated. In such an arrangement, the relative flexibility is also reversed, making the more distal portion less flexible instead of more flexible.

In FIG. 7, pattern 360 has circumferentially arranged pairs of large non-laminated sections 400. Adjacent pairs are staggered at 90° to create a highly flexible catheter. Many other patterns are possible, including differently sized and shaped sections of selectively varied lamination, differently sized and shaped spacing between non-laminated sections, pattern variations along the length of the catheter, and long regions or selected regions having no sections of selectively varied lamination. Such regions could be either fully laminated or have no lamination.

Typically, inner liner 30 and outer shell 34 are adhered to each other via thermoplastic bonding, with or without a tie layer, or via a bonding agent, such as glue, depending upon the materials used to make inner liner 30 and outer shell 34. Regions of selectively varied lamination may be formed between inner liner 30 and outer shell 34 by selectively interfering with the bonding between the two layers. These regions of selectively varied lamination have non-laminated sections with reduced bonding or no bonding at all between the inner liner 30 and outer shell 34.

In some embodiments, outer shell 34 may be formed about inner liner by the process of thermoplastic extrusion, which includes forcing shell material around and into thermal bonding contact with inner liner 30. Alternatively, outer shell 34 may be compression molded around inner liner 30 by the use of heat shrink tubing, which can be removed afterwards. Within regions of selectively varied lamination, non-laminated sections can be formed by selectively interfering with the bonding between inner liner 30 and outer shell 34. Interruption of thermal bonding in the non-laminated sections can be carried out, for example, by depositing an agent that interrupts bonding. Such agents include, but are not limited to, waxes and inks, which can be selectively applied to the outer surface of inner liner 30.

The bond-interrupting agent can be applied to inner liner 30 by known processes such as printing, spraying or dipping. The agent can be applied in a desired pattern, as by pad printing, roller pad printing, or spraying through a mask. The bond-interrupting agent can also be applied to completely cover the intended regions of selectively varied lamination. Then, the agent can be selectively removed or altered to create the desired pattern of bondable and non-bondable sections. Such selective removal or alteration of the bond-interrupting agent can be via photo or laser treatment, for example. Desirably, the agent is applied to a long piece of inner liner 30 by a continuous reel-to-reel process. If it is desired to vary the lamination along the length of each catheter 10, then the pattern of bond-interrupting agent can be repeated or reversed along the long piece of inner liner 30.

Next, outer shell 34 is extruded or molded over inner layer 30. In those sections where the bond-interrupting agent has been applied, there will be a reduced or non-existent thermal bond between outer shell 34 and inner liner 30. Next, the composite catheter tubing can be severed at desired cut points, forming multiple sub-assemblies of intended catheter length. Finally, catheters 10 are finished by securing the remaining components.

In some embodiments, thermal bonding between outer shell 34 and inner liner 30 is weak or non-existent because the materials are incompatible. Examples of this combination include nylon-based outer shells combined with polyolefin inner liners. In such cases, thermal bonding of the assembly can still be achieved by use of a tie layer interposed between outer shell 34 and inner liner 30. A tie layer is thermally bondable to both outer shell 34 and inner liner 30, acting like a hot-melt adhesive. In catheter construction, a tie layer can be applied over inner liner 30 by a continuous extrusion step or by use of heat shrink tubing, as described above. In one embodiment of the invention, a tie layer can be modified to include a pattern of open sections; each open section will not promote thermal bonding between outer shell 34 and inner liner 30. The openings can be formed in the tie layer by laser machining, for example, before or after the layer has been applied to inner liner 30.

As is well known in the field of medical catheters, there are material combinations wherein no thermal bonding can occur between inner liner 30 and outer shell 34, even with a tie layer. For example, if inner liner 30 comprises PTFE, then additional means must be used to permit bonding of the two layers. Typically, the outer surface of inner liner 30 is etched using either a laser or a strongly acidic etchant. After the liner surface has been prepared, an adhesive, such as an epoxy, can be used to bond inner liner 30 to outer shell 34. In one embodiment of the instant invention, the outer surface of a non-thermally bondable inner liner 30 can be treated to create a selected pattern of sections that can be glued to outer shell 34. These glue-able sections are interspersed with sections that cannot be glued to generate a catheter shaft having variable stiffness, as described in other embodiments above. Controlled etching can be used to form a pattern on the surface of inner liner 30. For example, a laser can be used to selectively etch desired sections. For example, a laser source can be switched off and on while the continuous inner liner 30 passes thereby. Alternatively, prior to etching, portions of inner liner 30 can be masked to cover the areas where laser or chemical etching is not desired. Upon completion of the etching process, the mask material is removed.

In some embodiments of the invention, the inner liner 30 is an ultra high molecular weight high density polyethylene (UHMW-HD PE), which is melt-extrudable. UHMW-HD PE, in contrast to PTFE, can be processed in a continuous, reel-to-reel fashion. UHMW-HD PE, however, is highly chemically resistant and, thus, cannot be chemically etched so as to create a surface that can bond to a polymer outer shell 34. A solution to this problem, however, is to utilize a laser, such as an excimer laser, to modify the surface of the UHMW-HD PE to enhance bonding between UHMW-HD PE and the outer shell 34.

In any of the above embodiments of the invention, an optional reinforcing section 32, such as a braid, can be created around etched inner liner 30 before outer shell 34 is formed. Reinforcing section 32 is typically porous so that any of the above-mentioned lamination processes can occur there through.

There are many benefits of having regions of selectively varied lamination in a catheter. For example, such a catheter possesses variation in the properties along the length of the catheter. These properties include, but are not limited to, catheter stiffness, curve retention, overall back-up support, and the like.

As illustrated in FIG. 4, catheter shaft 12 can optionally include groove 18, which is cut out of catheter shaft 12 near distal end 20 of catheter shaft 12, as described in U.S. Pat. No. 6,059,769, which is incorporated herein by reference in its entirety. Groove 18 provides flexibility at distal end 20 of catheter shaft 12 without compromising the durability and torsional strength of catheter shaft 12. Further, groove 18 functions as transitional region 21 between relatively stiff catheter shaft 12 and flexible tip 16. This prevents or reduces kinking and/or collapsing of medical catheter 10. As a result thereof, medical catheter 10 has improved tracking and movement in the vessel. Fill section 35 may be positioned in groove 18. An embodiment of the invention may combine filled groove 18 with one or more regions of selectively varied lamination to achieve a desirable combination of mechanical properties.

While the particular medical catheter 10 as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A medical catheter adapted for use within a body vessel, the medical catheter comprising:
   a tubular catheter shaft comprising an inner liner surrounded by an outer shell, the shaft having a distal end that fits within the body vessel;
   wherein the catheter shaft comprises at least one region of selectively varied lamination providing one or more areas of reduced bonding or no bonding at all between an outer surface of the inner liner and an inner surface of the outer shell; and
   wherein the selectively varied lamination includes one of the following:
   a) a thermoplastic bond between the inner liner and the outer shell wherein the one or more areas of reduced bonding or no bonding at all comprise a thermal bond inhibiting agent; or
   b) an adhesive bond layer between the inner liner and the outer shell, an adhesively bonded outer surface of the inner liner comprising a bond enhancing treatment; or
   c) a thermoplastic tie layer melt-bonded between the inner liner and the outer shell, the tie layer comprising one or more open sections to provide the one or more areas of reduced bonding or no bonding at all; or
   d) an adhesive layer bonding the inner liner to the outer shell, the adhesive layer comprising a pattern of bonded sections and non-bonded sections.

2. The medical catheter of claim 1 wherein at least one region of selectively varied lamination comprises diamond-shaped or oval-shaped non-laminated sections.

3. The medical catheter of claim 1 wherein at least one region of selectively varied lamination comprises non-laminated sections, wherein the size of the non-laminated sections increases towards the distal end.

4. The medical catheter of claim 3 wherein at least one region of selectively varied lamination comprises laminated sections between non-laminated sections, wherein the size of the laminated sections between the non-laminated sections decreases towards the distal end.

5. The medical catheter of claim 1 wherein at least one region of selectively varied lamination comprises non-laminated sections, wherein the non-laminated sections form circumferentially arranged pairs.

6. The medical catheter of claim 5 wherein adjacent pairs are staggered at 90°.

7. The medical catheter of claim 1 wherein the inner liner comprises polytetrafluoroethylene, high density polyethylene, or fluorinated ethylene propylene.

8. The medical catheter of claim 1 wherein the outer shell comprises nylon or nylon 12.

9. The medical catheter of claim 1 wherein the distal end of the catheter comprises at least one region of selectively varied lamination.

10. The medical catheter of claim 1 wherein the proximal end of the catheter comprises at least one region of selectively varied lamination.

11. The medical catheter of claim 1 wherein the region of selectively varied lamination is present throughout the length of the catheter.

12. The medical catheter of claim 1 wherein the inner liner is unfilled or low-loaded with filler, radiopaque material, or colorant.

13. The medical catheter of claim 1 wherein the outer shell is unfilled or low-loaded with filler, radiopaque material, or colorant.

14. The medical catheter of claim 1 wherein the inner liner and outer shell are unfilled or low-loaded with filler, radiopaque material, or colorant.

15. The medical catheter of claim 1 wherein at least one region of selectively varied lamination comprises non-laminated sections and laminated sections, and the inner liner comprises ultra high molecular weight high density polyethylene.

16. The medical catheter of claim 15 wherein the surface of the ultra high molecular weight high density polyethylene inner liner within the laminated sections has been modified with a laser.

17. A medical catheter adapted for use within a body vessel, the medical catheter comprising:
   a tubular catheter shaft comprising an inner liner surrounded by an outer shell, the shaft having a distal end that fits within the body vessel;
   wherein the catheter shaft comprises at least one region having a thermoplastic bond layer between the inner liner and the outer shell, the bond layer comprising one or more areas of reduced bonding or no bonding at all between the inner liner and the outer shell; and
   wherein the one or more areas of reduced bonding or no bonding at all comprise a thermal bond inhibiting ink or a thermal bond inhibiting wax.

* * * * *